United States Patent [19]

Maruyama

[11] Patent Number: 4,719,804
[45] Date of Patent: Jan. 19, 1988

[54] APPARATUS FOR TESTING PERFORMANCE OF CLAMP SCREW IN ELASTIC AND PLASTIC REGIONS

[75] Inventor: Kazuo Maruyama, Machida, Japan

[73] Assignee: Tokyo Institute of Technology, Tokyo, Japan

[21] Appl. No.: 896,274

[22] Filed: Aug. 14, 1986

[30] Foreign Application Priority Data

Aug. 19, 1985 [JP] Japan ................................ 60-181577

[51] Int. Cl.$^4$ ............................................. G01N 3/00
[52] U.S. Cl. ........................................ 73/794; 73/761
[58] Field of Search ................ 73/794, 795, 826, 847, 73/761

[56] References Cited

U.S. PATENT DOCUMENTS 3,354,705 11/1967 Dyer, Jr. ............................ 73/795 X
4,554,838 11/1985 Paus ...................................... 73/761

Primary Examiner—Jerry W. Myracle
Attorney, Agent, or Firm—Spencer & Frank

[57] ABSTRACT

An apparatus for testing performances of a screw consisting of a bolt and a nut in the plastic region under loading of an external force as well as in the elastic region. The apparatus comprises a load cell adapted for detecting thread torque, bearing torque, clamping torque and axial tension, nut tightening apparatus, apparatus for generating external force to be applied to the sample screw and an extensometer adapted for detecting twist angle and elongation of the bolt and revolution angle of the nut.

12 Claims, 10 Drawing Figures

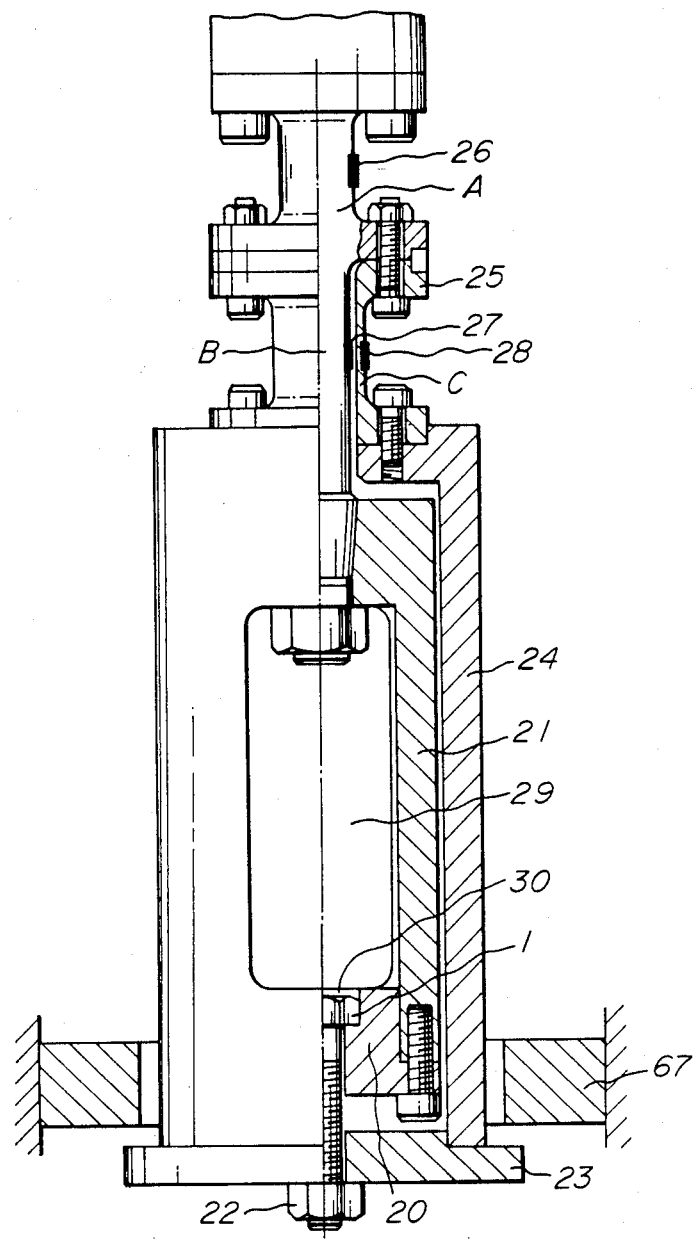
FIG_2

FIG_3A
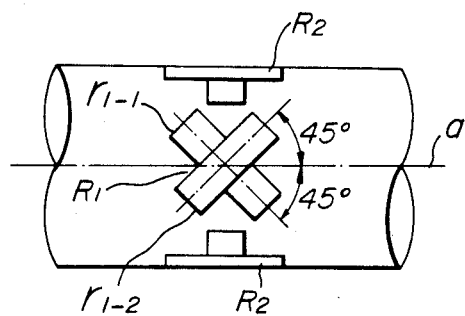
FIG_3B
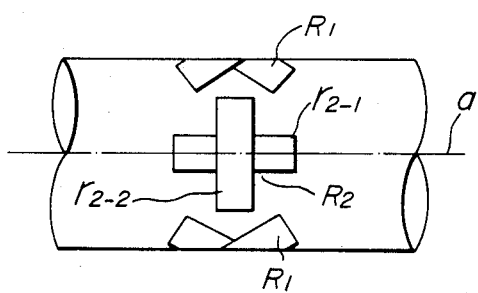

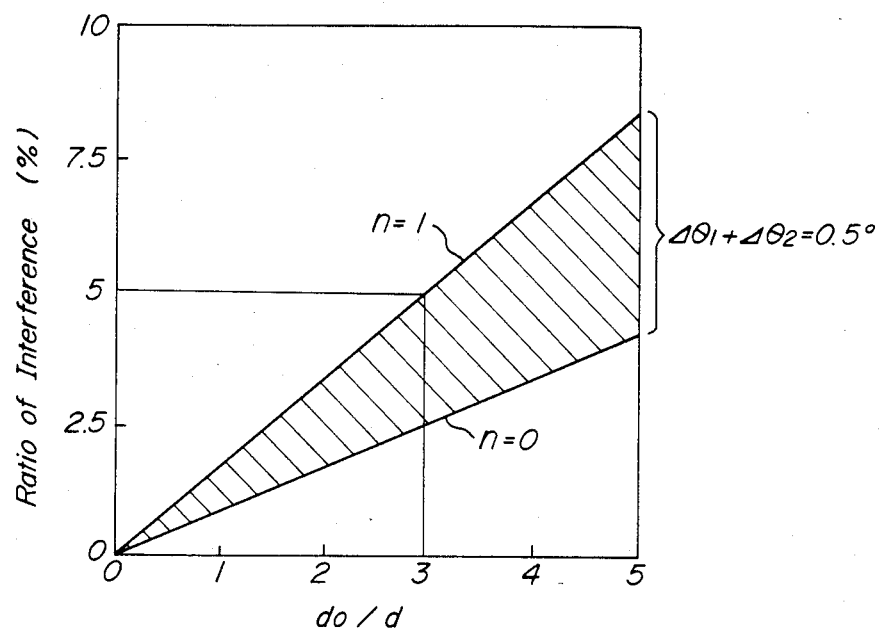
FIG_4

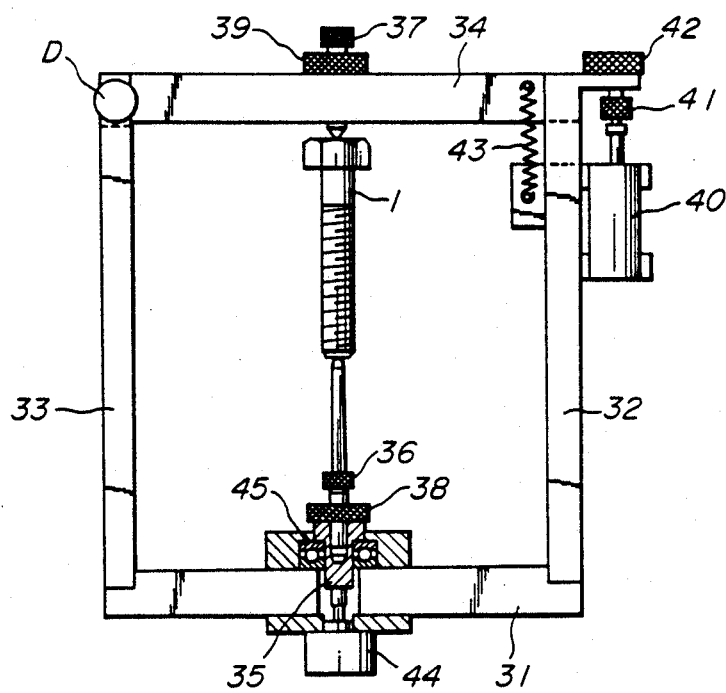
FIG_5

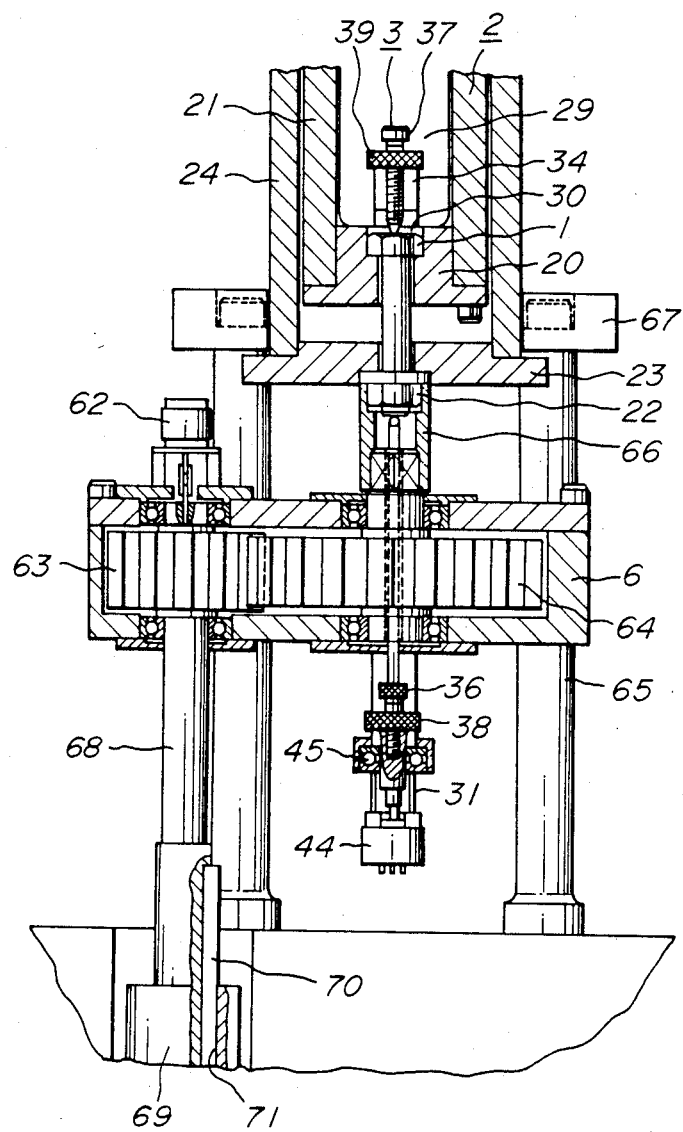
FIG_6

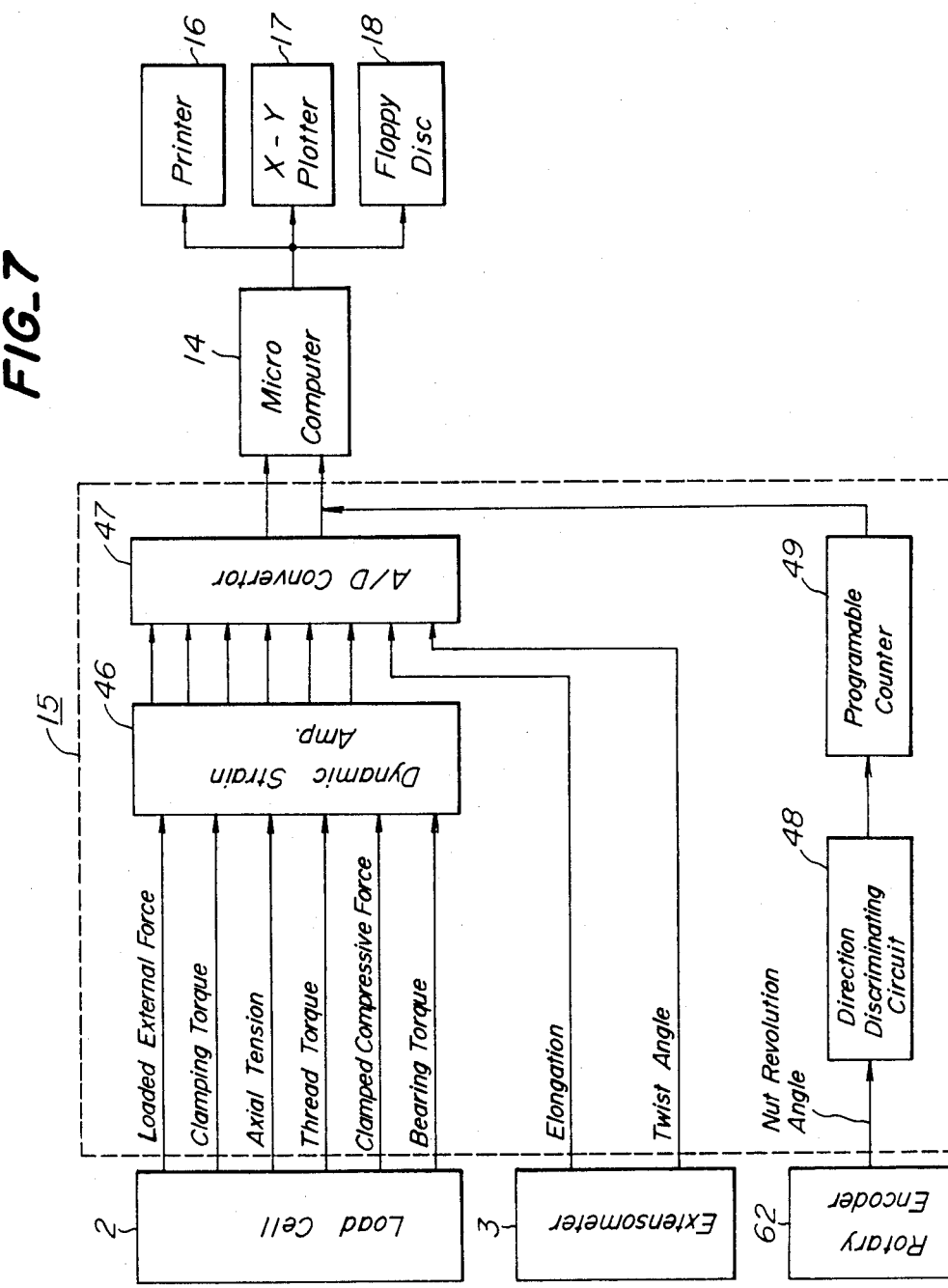

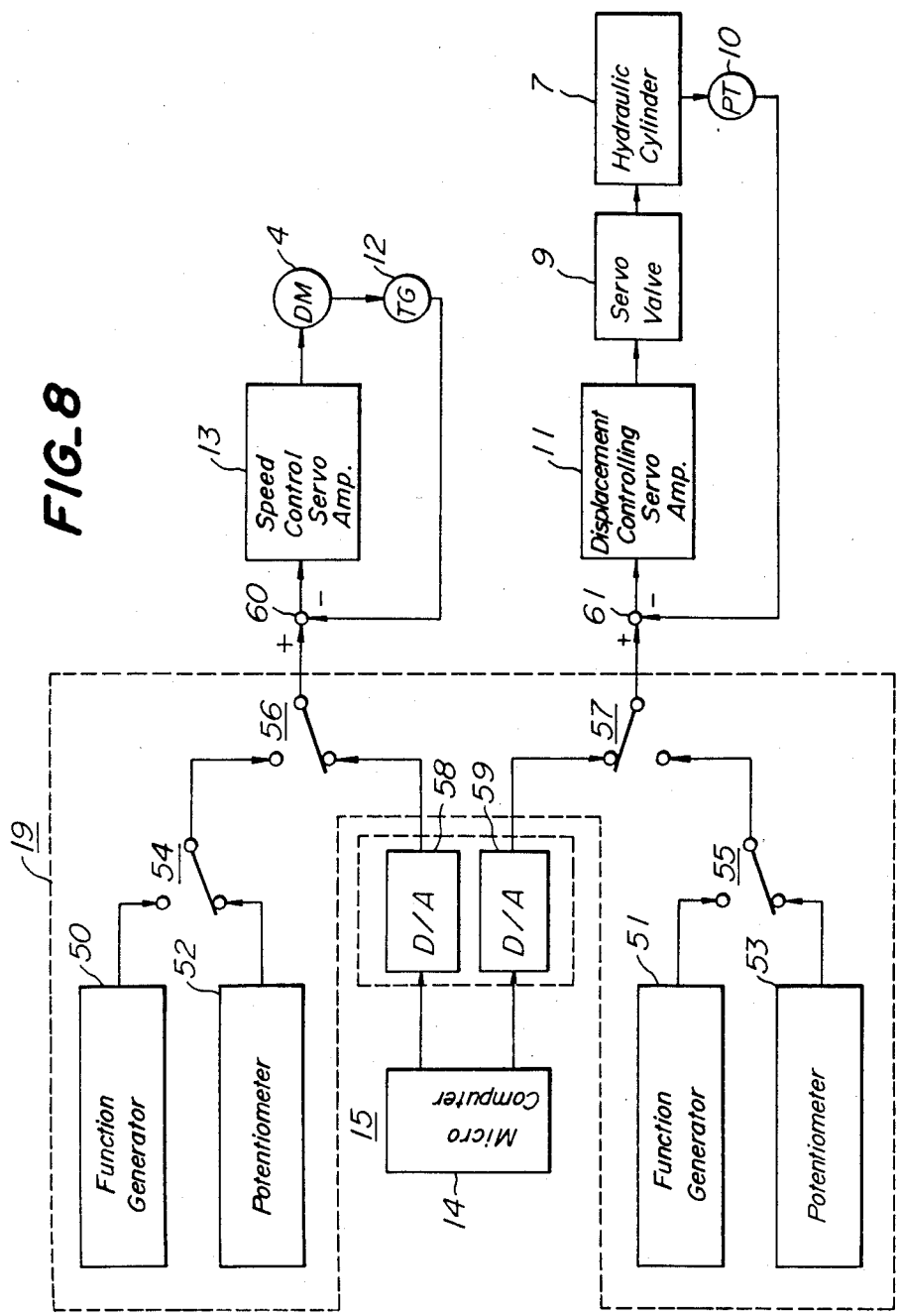

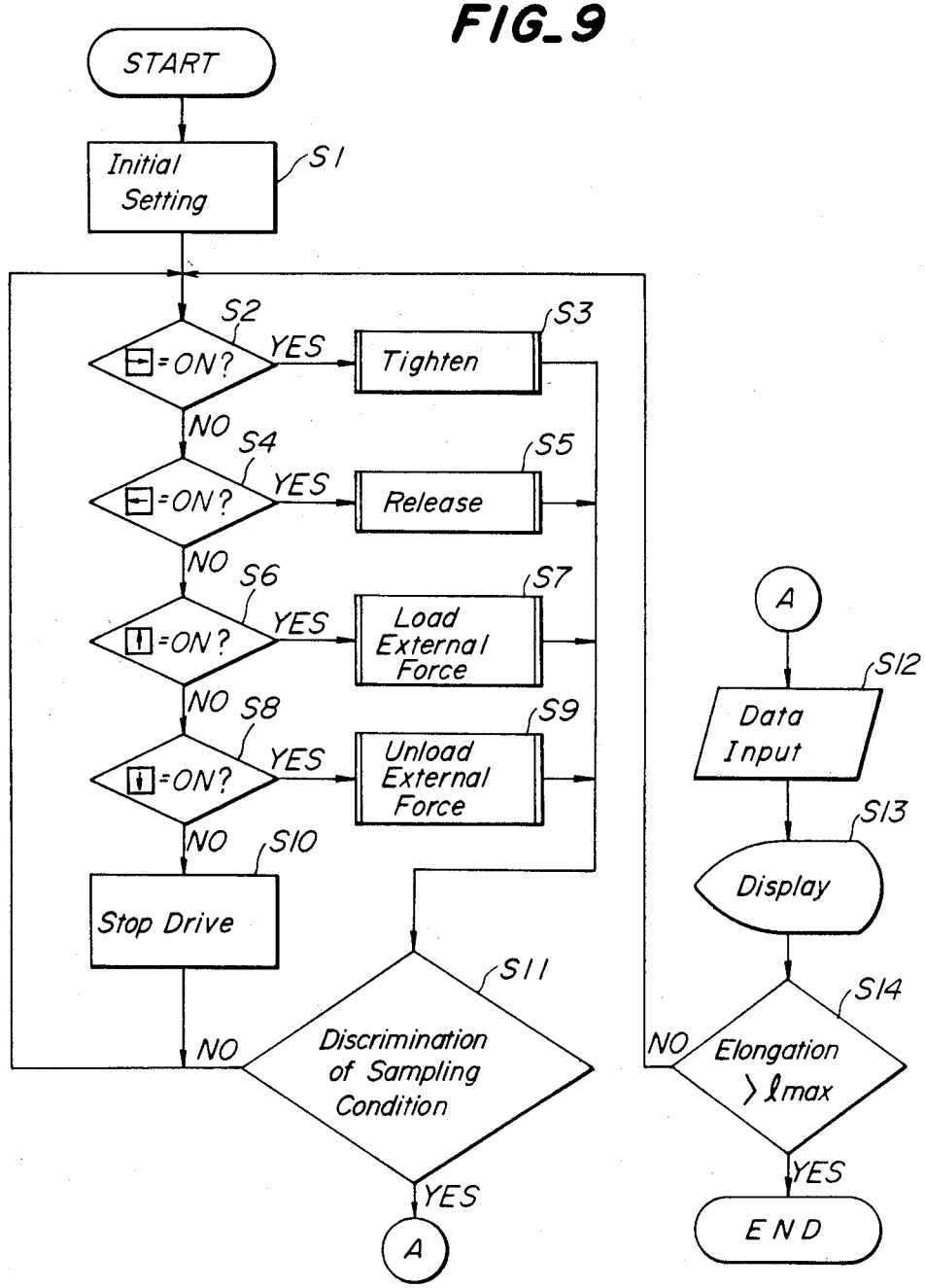
FIG_9

APPARATUS FOR TESTING PERFORMANCE OF CLAMP SCREW IN ELASTIC AND PLASTIC REGIONS

BACKGROUND OF THE INVENTION

1. Field of the Invention

The present invention relates to an apparatus for testing a clamp screw consisting of a bolt and a nut, particularly an apparatus for testing performance of a clamp screw in its elastic and plastic regions. The apparatus enables the measurement of any kind of required performance of a clamp screw in its elastic and plastic regions in order to permit tightening the clamp screw in the plastic region as well as in the conventional elastic region.

2. Related Art Statement

In general, screw parts such as bolts and nuts have been tested for quality certification by use of material tension testing machines and screw clamp testing machines, and there are measured various performance criteria for a clamping screw such as clamping torque, bearing torque, thread torque, axial tension and the twisting and revolution angle of a bolt and nut in the elastic region.

However, conventional material tension testing machines have a disadvantage in that elongation generated by clamping a bolt cannot precisely be measured. Further, conventinal screw clamp testing machines have such disadvantage that the elongation and twist angle of a clamped bolt up to break down cannot be measured, and in the actual use of a clamp screw, in external force will be applied to the clamp screw after it is clamped, but the testing machine cannot perform a test corresponding to the external force which will be applied to the clamped screw.

On the other hand, recent technical improvements are directed to the provision of highly precise and compact machines, and this has resulted in a requirement for highly reliable and small clamp screws which are inevitable to assemble the machineries.

That is, conventional clamp screws are designed for clamping in the elastic region so that even in the case of loading with an external force, the axial tension subjected by to whom the screw parts such as bolts and nuts are subjected does not exceed the limit of elasticity with a sufficient allowance. Therefor its working efficiency in strength is limited to 40–50%, which is a redundant design. Further, as to reliability, the conventional clamp screw designed for clamping in the elastic region has the initial clamp force design value which has a dispersed large difference from an actual value. On the contrary, the plastic region clamping of a clamp screw is to clamp over the yield point of the screw parts, so that its use efficiency in strength reaches 80–90%, screw parts can be miniaturized as compared with the elastic region clamping, and dispersion of the clamp force can be more reduced more than in the case of elastic region clamping. Thus, improvement of various performances can be expected.

However, the behavior of a clamp screw in the case of clamping in the plastic region is still unsolved or unknown, and there are many uncertain factors involved when precisely clamping in the plastic region. In particularly, the behavior of a screw when it is subjected to an external force after being clamped is not well-known in spite of its being an extremely important problem.

SUMMARY OF THE INVENTION

An object of the present invention is to experimentally solve the above mentioned problems.

An object of the present invention is to provide an improved apparatus for testing all of the performance criteria of a clamp screw in its elastic and plastic regions by clarifying plastic phenomenona of the clamp screw from a clamped condition in the plastic region to a loaded condition subjected to an external force.

An object of the present invention is to provide an apparatus for testing a clamp screw having both a functions of the conventional material tension testing machine and a conventional screw clamp testing machine and enabling the measurement of clamping torque, bearing torque, thread torque, bolt axial tension, external force, bolt elongation and twist angle, compressive force of an article to be clamped, nut revolution angle and the like and to control these measurements by means of a computer so as to promptly process the measured data and to output as a display.

An apparatus for testing the performance of a clamp screw according to the present invention comprises a load cell including an opening having a bolt receiving bore for receiving a sample screw consisting of a bolt and a nut, a bolt retainer for engaging the head of the bolt to prevent the bolt from rotating when the nut is tightened on the bolt inserted in the bolt receiving bore, a bearing plate for engaging the nut tightened on the bolt, first strain detecting means for detecting thread torque and axial tension applied to the bolt retainer, second strain detecting means for detecting bearing torque and axial tension applied to the bearing plate and third strain detecting means for detecting clamping torque consisting of the sum of the thread torque and the bearing torque and being so arranged that the bolt retainer and the bearing plate are separated from each other along the axis of the clamp screw by an external force; nut tightening means for tightening said nut; external force generating means for generating said external force; and extensometer including a stationary frame provided with twist detecting means for detecting the twist angle of said bolt by abutting on the tip end of said bolt, a movable frame engage with said load cell through said opening and rotated with respect to said stationary frame in accordance with the axial displacement of the head of said bolt, and means for detecting elongation of said bolt in accordance with the rotation of said movable frame.

According to such apparatus for testing the performance of a clamp screw of the invention, a single testing apparatus can perform almost all static tests and dynamic tests which have been carried out by both conventional material tension testing and conventional screw clamp testing machines, and it becomes possible to complete a series of tests in a short time such as about 10 minutes inclusive of a bolt-nut test in case of applying external force in the axial direction after clamping which is impossible with conventional testing machines, so that the apparatus according to the invention is extremely economical.

BRIEF DESCRIPTION OF THE DRAWINGS

For a better understanding of the invention, reference is made to the accompanying drawings, in which:

FIG. 2 is a side elevational view showing a load cell in the apparatus partly in section;

FIGS. 3A and 3B are diagrammatic views of a strain detector in the load cell;

FIG. 4 is a graph showing the relationship between the ratio of the outer diameter of the head shaft secured to the inner frame to the nominal diameter of the sample clamp screw and the ratio of interference of the axial tension to the thread torque of the sample clamp screw;

FIG. 5 is a side elevational view of an extensometer in the apparatus of the invention;

FIG. 6 is a sectional side view of the load cell and the extensometer with the sample clamp screw loaded therein;

FIG. 7 is a block diagram showing the arrangement of a processing unit in the apparatus;

FIG. 8 is a block diagram showing the arrangement of the control for the machine portion in the apparatus; and FIG. 9 is a flow chart showing one example of a process for testing the performance of a clamp screw in the apparatus of the invention.

DESCRIPTION OF THE PREFERRED EMBODIMENTS

Figure 1:
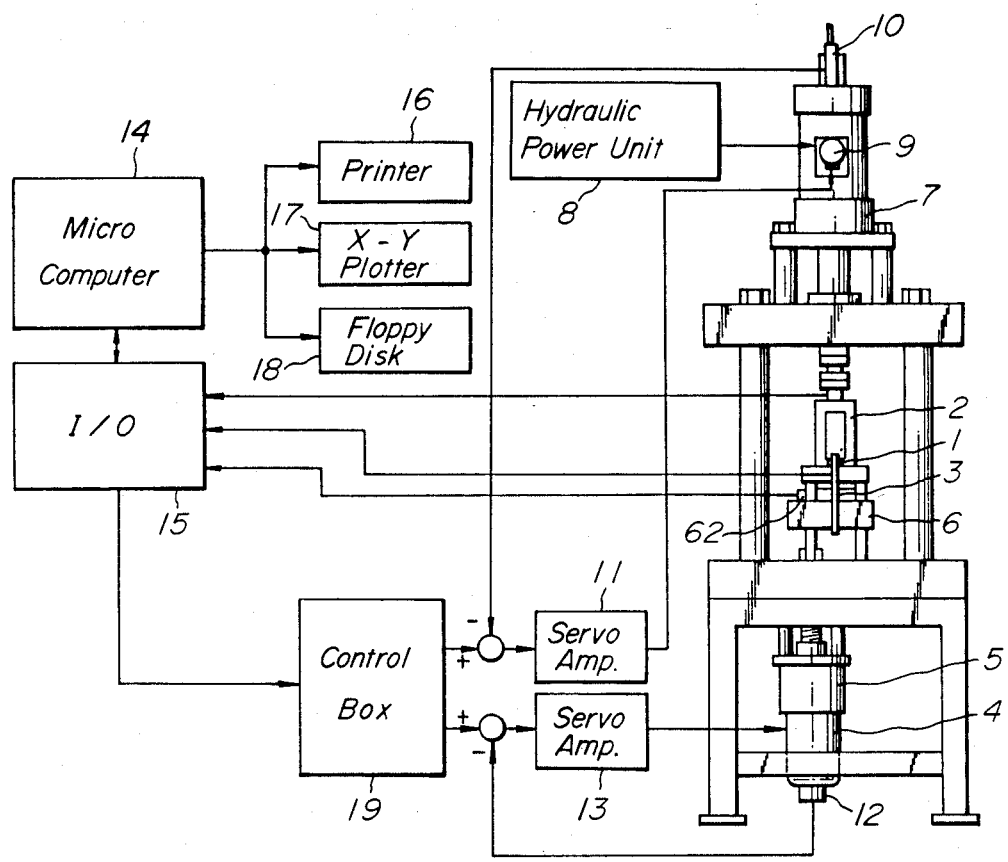
FIG. 1 is a block diagram showing the general arrangement of the apparatus for testing the performance of a clamp screw of the present invention.

In FIG. 1 is shown the general outline of the apparatus for testing the performance of a clamp screw according to the invention.

The apparatus according to the invention consists of a machine portion shown on the right side, a machine control portion shown in the center portion and a processing portion shown in the left side of FIG. 1. The machine portion is the main portion of the apparatus according to the invention and includes a load cell 2 and an extensometer 3 arranged in opposed positions for mounting a sample clamp screw, that is, a bolt-nut 1 therebetween.

The load cell 2 is constructed as described later on with reference to FIG. 2 and can detect each of thread torque, bearing torque, clamping torque, axial tension and external force applied to the bolt-nut 1, respectively, and the extensometer 3 is constructed as described later on with reference to FIG. 3 and can detect the elongation and twist angle of the bolt generated by clamping the bolt-nut 1.

In order to apply a clamping torque to the bolt-nut 1 fixed to load cell 2 and extensometer 3, successive rotation of a DC servomotor 4 driven by the servo system is transmitted to a socket wrench through reduction gears 5 and 6 to clamp the nut on a bearing plate of the load cell 2. On the other hand, in order to apply an external force in the axial direction to the bolt-nut 1 under a clamped condition, the bearing plate is rigidly secured in the axial direction and the head of the bolt is fitted to an inner frame of the load cell 2. An external force is applied to the inner frame in a direction away from the bearing plate by means of a hydraulic cylinder 7 which is connected to the inner frame. The hydraulic cylinder 7 is driven by the a hydraulic power unit 8 through a servo valve 9 controlled by servo system which will be described later on.

In the machine portion having the above-described construction, various data such as each kind of torque and axial tension applied to the sample bolt-nut 1 are taken from various location including out of the load cell 2, the rotary encoder 62 combined with the reduction gear 6, the tachometer generator 12 combined with the DC servomotor 4, the potentiometer 10 combined with the hydraulic cylinder 7. The data are fed back to the machine control portion consisting of a control box 19 and servo amplifiers 11, 13 through a signal input-output device 15 of the processing unit to control the DC servomotor 4 and the hydraulic cylinder 7. At the same time, above various data are supplied to a microcomputer 14 through the signal input-output device 15, to provide various characteristic data showing desired performance of clamp screw in the plastic region. These data are automatically recorded by recording devices, such as a printer 16, an X-Y plotter 17, a floppy disk 18 and the like.

Next, FIG. 2 shows an embodiment of the load cell 2 which is one main portion in the apparatus for testing performance of a screw according to the invention. The load cell 2 illustrated in FIG. 2 is approximately cylindrical and provided with an opening 29 having a bolt receiving bore 30 at the center thereof. The bottom surface of the opening 29 is formed by a bolt retainer 20, and the retainer has a bore for fitting a hexagonal head of the bolt 1 for preventing the sample bolt 1 from rotation, and the bottom flange of the bolt retainer 20 is secured to the lower end of a cylindrical inner frame 21 by screws. A head shaft B fixed to the frame 21 is fitted to a head shaft C of an outer frame 24 and the outer diameter of the head shaft B of the inner frame 21 is limited to no more than three times the diameter of the sample clamp screw, for the reason mentioned later on. The cylindrical outer frame 24 surrounds the outer periphery of the inner frame 21 and extends downwardly from the inner frame 21, so as to abut the lower end thereof to a bearing plate 23 and to clamp the bearing plate with the bolt retainer 20 by tightening the sample nut 22 on the sample bolt 1 mounted in the load cell 2. Further, in order to fix the sample nut easily, a tightening box 6 consisting of a gear box for tightening the nut shown in FIG. 1, is vertically slidable relative to the reduction gear 5 consisting of a similar gear box, as will be explained with reference to FIG. 6. In case of combining with the extensometer 3, a driving shaft of the reduction gear 5 is separated from the clamping shaft of the tightening box 6. The clamping shaft is hollow so as to insert an adjusting screw for adjusting the end position of the sample bolt 1 mounted on the extensometer 3.

When the sample bolt 1 and the sample nut 22 are mounted on and clamped with the load cell 2 constructed as described above, the thread torque and the axial tension applied to the bolt 1 are transmitted to the inner frame 21 through the bolt retainer 20, and measured by a strain detector 27 provided in the shaft B. At the same time, the bearing torque applied to the bearing plate 23 by the nut 22 and the clamping compression force are transmitted as one axial tension to the outer frame 24 abutted to the bearing plate 23 at the lower end and measured by a strain detector 28 provided in the shaft C. Shaft B of the inner frame 21 and shaft C of the outer frame 24 are secured to each other at the flange portion 25 by means of screws so as to measure the clamping torque which is the sum of the thread torque to the inner frame 21 and the bearing torque to the outer frame 24 by the strain detector 26 provided in the upper shaft A above the flange portion 25. The strain detector 26 provided in the shaft A can also measure the external force in the axial direction applied by the hydraulic cylinder 7 mounted at the upper portion of the shaft A as illustrated in FIG. 1. In addition, each of the strain detectors is constructed to measure respective strain by an electric resistance change due to strain produced on the applying surface of a cross gauge assembled by two strain gauges affixed in the orthogonal position relative to each other. Each of the strain gauges may consist of a resistance wire formed in zigzag shape. In order to detect the torque in the embodiment, two torque detecting cross gauges $R_1$ are affixed to the surface of the head shaft at the diametrically opposite sides of the head shaft in axial symmetry and are arranged such that the two strain gauges $r_{1-1}$ and $r_{1-2}$ in each of the cross gauges $R_1$ are inclined at an angle of 45° to the axis a of the head shaft as shown in FIG. 3A and are assembled in a bridge circuit for detection. On the other hand, in order to detect the axial tension, two axial tension detecting cross gauges $R_2$ are affixed to the surface of the head shaft at positions shifted in the circumferential direction by an angle of 90° from each of the positions of the torque detecting cross gauges $R_1$ and also at diametrically opposite sides of the head shaft are in axial symmetry. In this arrangement the axis of one $r_{2-1}$ of the strain gauges $r_{2-1}$ and $r_{2-2}$ in each of the cross gauges $R_2$ is aligned with the axis a of the head shaft as shown in FIG. 3B.

Further, if an external force in the axial direction is applied to the shaft A upwardly, the inner frame 21 and the outer frame 24 are integrally pulled upward, and the bolt retainer 20 engaged with the inner frame 21 is therefore pulled up to pull the sample bolt 1 upward. However, the bearing plate 23 is abutted to the lower end of the outer frame 24 which abuts a stopper plate 67 fixed to the outer periphery thereof, so that the external force is applied to the bolt retainer 20 to separate from the bearing plate 23 and therefore the force is finally applied to the clamped sample bolt and nut in such a direction that the bolt and the nut are separated from each other in the axial direction.

Further, in the strain detectors 27 and 28 affixed to the head shafts B and C of the load cell 2, as described with reference to FIG. 3, the thread torque and the bearing torque detected by the cross gauges including two strain gauges orthogonal to each other and at an angle of 45° to the axis of the head shaft are separated from the axial tension detected by the cross gauges including the two strain gauges one of which is aligned with the axis of the head shaft and taken out independently. Accordingly, if the angle of affixing the strain gauges relative to the axial direction inevitably has an error, there is caused interference of the axial tension to the thread torque and the bearing torque and as a result, an error is produced in the measured value.

When considering a ratio of interference representing the degree of the interference of the axial tension with the thread torque and the bearing torque, if two resistance wire strain gauges symmetrically orthogonal to each other on the diametrically opposite sides of each of the cylindrical head shafts of the load cell are secured at an angle of 45° with respect to the axial direction, it is assumed that the angle deviations in the front and rear sides are $\Delta\theta_1$ and $\Delta\theta_2$, respectively. Strain output $\epsilon_0$ of such four strain gauges generated by applied torque T may be represented by the following equation (1).

$$\epsilon_o = \frac{32T}{\pi G d_o^3(1 - n^4)} \quad (1)$$

where G is modulus of elasticity in shear, $d_0$ is the outer diameter of the cylindrical head shaft, and n is the ratio of the inner diameter $d_1$ to the outer diameter $d_0$ of the cylindrical head shaft.

To the strain output $\epsilon_0$ is added an interference strain $\epsilon_{0\theta}$ of the axial tension $F_f$ to the torque represented as the following equation (2) if the angle of the affixed strain gauge to the axis (a) has deviation of $\Delta\theta_1$ and $\Delta\theta_2$ and at the same time a strain $\epsilon_f$ in the axial direction is caused by the axial tension.

$$\epsilon_{0\theta} = \tfrac{1}{4}\epsilon_f\{\cos 2(45 - \Delta\theta_1) + \cos 2(45 - \Delta\theta_2) - \cos 2(45 + \Delta\theta_1) - \cos 2(45 + \Delta\theta_2)\} \quad (2)$$

$$= \epsilon_f(\sin 2\Delta\theta_1 + \sin 2\Delta\theta_2)$$

On the other hand, the ratio of interference is represented by a ratio of strain $\Delta_{0\theta}$ by axial tension $F_f$ to strain $\epsilon_s$ or strain $\epsilon_w$ by the thread torque $T_s$ or the bearing torque $T_w$. Thus, the axial tension $F_f$ and the clamping torque $T_f$ are in relation of the following equation (3).

$$T_f = KF_f d \quad (3)$$

Where, K is the torque coefficient and d is the nominal diameter of screw.

About 50% of the clamping torque $T_f$ becomes the thread torque $T_s$ or the bearing torque $T_w$, and these torques are in relation to the following equation (4).

$$T_s \approx T_w \approx 0.5\, T_f \quad (4)$$

Therefore, if considering the thread torque $T_s$ or the bearing torque $T_w$ as the torque, a strain gauge output $\epsilon_{ot}$ is represented as the following equation (5) by combining the equation (1) with the equation (4).

$$\epsilon_{ot} = \frac{32 \cdot 0.5 T_f}{\pi G d_o^3(1 - n^4)} \quad (5)$$

On the other hand, the strain $\epsilon_f$ by the axial tension is represented as the following equation (6) by using the equation (3).

$$\epsilon_f = \frac{F_f}{AE} = \frac{\frac{T_f}{Kd}}{\tfrac{1}{4}\pi(d_o^2 - d_1^2)E} = \frac{4T_f}{\pi EKd(d_o^2 - d_1^2)} \quad (6)$$

where, A is the cross-sectional area of the cylindrical head shaft, $d_1$ is the inner diameter of the cylindrical head shaft and E is the modulus of elasticity in tension and compression (Young's modulus).

The interference strain $\epsilon_{0\theta}$ which is to be added to the gauge output strain $\epsilon_{0t}$ of the equation (5) can be calculated by the equation (2) by using the axial strain $\epsilon_f$ of the axial tension according to the equation (6) when the deviation of affixing angle of the strain gauges are $\Delta\theta_1$ and $\Delta\theta_2$. Accordingly, a ratio of interference $\epsilon_{0\theta}/\epsilon_{0t}$ can be represented by the following equation (7).

$$\text{(ratio of interference)} = \frac{Gd_0(1 + n^2)}{4EKd} (\sin 2\Delta\theta_1 + \sin 2\Delta\theta_2) \quad (7)$$

When the unit of the angle is converted from degrees (°) to radians to modify the equation (7), the ratio of interference is represented as the following equation (8).

$$\text{(Ratio of interference)} = \quad (8)$$

$$\frac{Gd_0(1 + n^2)}{4EKd}\left(\sin\frac{\pi \cdot \Delta\theta_1}{90} + \sin\frac{\pi \cdot \Delta\theta_2}{90}\right)$$

$$\simeq \frac{Gd_0(1 + n^2)}{4EKd} \cdot \frac{\pi}{90} \cdot (\Delta\theta_1 + \Delta\theta_2)$$

where, the modulus of elasticity in shear G can be expressed as follows by using Poisson's ratio v.

$$G = \frac{E}{2(1 + v)}$$

Therefore, the ratio of interference is represented by the following equation (9).

$$\text{(ratio of interference)} = \quad (9)$$

$$\frac{\pi(1 + n^2)}{4 \cdot 180 \cdot (1 + v) \cdot K}\left(\frac{d_0}{d}\right) \cdot (\Delta\theta_1 + \Delta\theta_2)$$

Therefore, the ratio of interference is proportioned to a ratio of the outer diameter $d_0$ of the head shaft B to the nominal diameter d of the screw.

In the above equation (9), if it is assumed that $0 \leq n < 1$, torque coefficient K is 0.2.

Young's modulus is 21000 kgf/mm² and Poisson's ratio v is 0.3, the ratio of interference is represented by the following equation (10).

$$\text{(ratio of interference)} = 0.01678 \cdot (1 + n^2)\left(\frac{d_0}{d}\right) \cdot (\Delta\theta_1 + \Delta\theta_2) \quad (10)$$

The variation of the ratio of interference to the variation of the ratio $d_0/d$ of the outer diameter $d_0$ of the load cell head shaft B to the nominal diameter d of the sample clamp screw when the deviation of affixing angle of the strain gauge ($\Delta\theta_1 + \Delta\theta_2$) is limited to less than 0.5° is shown in FIG. 4 by hatched portion. Therefore, in order to restrain the ratio of interference of the axial tension to the torque to lower than 5%, the ratio of $d_0/d$ must be lower than three so that the outer diameter $d_0$ of the load cell head shaft B does not exceed three times the nominal diameter d of the sample clamp screw.

FIG. 5 shows an embodiment of the extensometer 3 which is one main portion in the apparatus for testing performance of a screw according to the invention. The extensometer 3 illustrated in FIG. 5 includes a stationary frame 31 extending in the transverse direction. At the center of the frame 31 is provided a device for adjusting the length of the sample clamp bolt. This adjusting device can adjust the position of the tip of the sample bolt 1 mounted in the load cell 2 cooperating with the extensometer 3 and set the reference point for measurement of the elongation of bolt 1. To the opposite ends of the frame 31 is connected a pair of vertical stationary frames 32 and 33 having the same length. A movable frame 34 is pivoted at D to the top end of the vertical stationary frame 33 and is provided with a device for adjusting the length of the sample bolt 1 at the central portion of the movable frame 34 so as to move vertically thereby corresponding to the axial displacement of the head of the bolt 1, i.e., the length of the bolt 1 cooperates with the device for adjusting length of the bolt on the transverse stationary frame 31 thereby providing a means for detecting elongation of the bolt between the movable frame 34 and the other vertical stationary frame 32.

In operation, the extensometer 3 is combined with the load cell 2 to measure the elongation of the sample clamp screw 1 mounted on the load cell 2. Thus, the movable frame 34 is rotated about the fulcrum D to open the extensometer and then the sample bolt 1 is inserted into and extended through the opening 29 of the load cell 2. The bolt length adjusting device on the movable frame 34 and the transverse stationary frame 31 are adjusted to abut to the head and the tip end, respectively, and the movable frame 34 is engaged with the top end of the vertical stationary frame 32. Therefore, as shown in FIG. 6, the load cell 2 and the extensometer are combined so as to engage the sample bolt 1 at the opposite sides. That is, in the embodiment shown in FIG. 6, the movable frame 34 of the extensometer 3 extends through the opening 29 of the load cell 2 normal to the plane of the drawing so that the bolt length adjusting screw 37 on the movable frame 34 can abut the head of the sample bolt 1 inserted in the bolt receiving bore 30. The bolt length adjusting screw 36 on the lower stationary frame 31 extending normal to the plane of the drawing can also abut the tip of the sample bolt and thus the load cell 2 and the extensometer 3 engage with the sample bolt 1 at the upper and lower sides, respectively.

The lower bolt length adjusting screw 36 extends through a hollow shaft of a large gear 64 in the tightening gear-box 6 abutting the tip of the sample bolt 1 and has a sufficient length to permit movement of the gear box 6 in the vertical direction along a guide 65 for engaging and disengaging the sample nut 22 with the sample bolt 1 easily. The large gear 64 is constantly engaged with the small gear 63 in the gear box 6. The small gear has a shaft 68 which is rigidly secured thereto and extends downwardly through the gear box 6. The shaft 68 is connected to an output shaft 69 of the reduction gear 5 by means of a vertically elongated key 70 and a slot in the shaft 69 for permitting the vertical slide movement of the gear box 6.

The bolt length adjusting device on the stationary frame 31 includes a bolt length adjusting screw 36. The screw 36 is threadedly engaged with a rotary shaft 35 rotatably supported by means of a thrust bearing 45 in the frame and is locked to the rotary shaft 35 by means of a locking nut 38 to set the position of the tip end of the sample bolt 1 in the axial direction. A twist detection potentiometer 44 is connected to the rotary shaft 35 for detecting the twist angle of the bolt 1. The bolt length adjusting device on the movable frame 34 includes a bolt length adjusting screw 37 which is threadedly engaged with a threaded hole in the movable frame 34. The adjusting screw 37 is locked to the movable frame 34 by means of a locking nut 39 in such a position that the tip end of the adjusting screw 37 abuts the head of the bolt 1 accurately, thereby to displace the tip of the adjusting screw in the vertical direction when the movable frame 34 is rotated about the fulcrum D corresponding to the elongation of the bolt 1.

There is a device for detecting elongation of the sample bolt between the movable frame 34 and the stationary frame 31. This detecting device includes an adjusting screw 41 for adjusting the zero point of the potentiometer. The adjusting screw 41 is threadedly engaged with a threaded hole in the free end portion of the movable frame 34 and is locked in an adjusted position by means of a locking nut 42 after a potentiometer 40 for detecting elongation of bolt has been set to the zero point by adjusting the screw 41 in the initial condition of elongation of the sample bolt. The potentiometer 40 is secured to the upper end portion of the vertical stationary frame 32 and is in contact with the tip end of the adjusting screw 41. The end portions of the frames 31 and 34 are pulled to each other to remove any gap in the contact condition of the adjusting screw 41.

FIG. 7 shows a detailed embodiment of the processing unit shown in FIG. 1. In the processing unit arranged as shown in FIG. 7, the various data such as loaded external force, clamping torque, axial tension, thread torque, clamping compression and bearing torque from the strain detector in the load cell 2 are amplified through a dynamic strain amplifier 46 in the signal input-output device 15 and supplied to an A/D converter 47 together with each data of elongation of bolt and twist angle from each of potentiometers 40 and 44 in the extensometer 3 to convert them to digital data, respectively. These digital data are transmitted to the microcomputer 14 together with data of nut revolution angle obtained through the direction discriminating circuit 48 and the programmable counter 49 from the rotary encoder 62 directly connected to the drive shaft of the reduction gear 6 in the nut revolution drive system to form each kind of characteristic curves representing various performances of clamping screw in the plastic region and then to record in either a printer 16, an X-Y plotter 17 or a flopy disc 18.

FIG. 8 shows an embodiment of the machinery controlling portion shown in FIG. 1. The machinery controlling portion arranged as shown includes a DC servomotor for the tightening mechanism and a hydraulic cylinder for the external force loading mechanism. The servomotor and the hydraulic cylinder may be servo controlled. The DC servomotor controls the speed for tightening the sample screw and the hydraulic cylinder controls displacement produced by the external force. The controlling data from the control box 19 shown in FIG. 1 are supplied to the DC servomotor 4 through the speed controlling servo amplifier 13 and to the hydraulic cylinder 7 through the servo amplifier 11 and the servo valve 9. The resulting displacements based on the tightening speed of screw and the loading of external force are detected by the tachometer generator 12 and the potentiometer 10 and fed back to the input of the servo amplifiers 13 and 11 so as to set the necessary operational conditions for each kind of performance test. The control data for setting of the operational conditions are provided in a microcomputer mode from the microcomputer 14 through D/A converters 58, 59 and switches 56, 57 in the control box 19 to the speed control system and the displacement control system and are also provided in a manual mode by switching function generators 50 and 51 and potentiometers 52 and 53 by means of switches 54 and 55.

FIG. 9 is a flow chart representing a measurement control program for a series of clamp screw performance tests wherein each kind of data from the screw testing machinery portion controlled by the machinery control portion are processed by the processing unit. In the illustrated measurement control program, an operator monitors various data on the display representing conditions of the sample screw provided by the load cell 2, the extensometer 3 and the rotary encoder 62. The control program sets the initial condition at step $S_1$, and then at steps $S_2$, $S_4$, $S_6$ and $S_8$, detects whether a cursor key on the key board is operated or not. If the cursor key is operated, a nut revolution speed command voltage or a displacement command voltage for the hydraulic cylinder corresponding to the operated cursor key is outputted to perform a subroutine of tightening, releasing, external force loading or unloading for the sample screw at steps of $S_3$, $S_5$, $S_7$ and $S_9$, and then the programs checks the clamping torque and the increment of displacement corresponding to the control value at step 1. If any significant increment is not detected by the program the above control steps are repeated. The various data obtained from variations in the above operations are inputted to the computer at step 12. The results of the above processing are monitored on the display at step 13 and the performance test is repeated until it is estimated that the elongation in the plastic region exceeds the given condition at step 14.

With the above construction of the apparatus for testing performance of a clamp screw of the invention, a tension test and a clamp test for combined bolt and nut and a test carried by applying an external force in the axial direction for combined and clamped bolt and nut can be carried out in the elastic and plastic regions of the sample bolt and nut to detect thread torque, bearing torque, clamp torque, bolt compression force caused by the tightening of the nut, revolution angle of nut, elongation and twist angle of the bolt and axial tension in each of conditions. These detected data are processed by the computer to provide screw performance information which may be recorded on a printer, X-Y plotter and/or floppy disc. The clamp test may be carried out in accordance with the torque control method, the turn of the nut method and, the torque gradient control method as well as others.

It is seen from the above description that according to the present invention, it becomes possible to perform a series of tests in the elastic and plastic regions for applying external force in the axial direction to a sample after it is clamped which was impossible by the conventional testing machines. Further the tension and clamp tests for bolt and nut can be performed by use of a single testing apparatus in an extremely economical manner.

What is claimed is:

1. An apparatus for testing performance of a screw, comprising
a load cell including an opening having a bolt receiving bore for receiving a sample screw consisting of a bolt and a nut, a bolt retainer for engaging the head of the bolt to prevent the bolt from rotating when the nut is tightened on the bolt inserted in the bolt receiving bore, a bearing plate for engaging the nut tightened on the bolt, first strain detecting means for detecting thread torque and axial tension applied to the bolt retainer, second strain detecting means for detecting bearing torque and axial tension applied to the bearing plate and third strain detecting means for detecting clamping torque consisting of the sum of the thread torque and the bearing torque and being such arranged that the bolt retainer and the bearing plate are separated from each other along the axis of the clamp screw by an external force;

nut tightening means for tightening the nut;

means for generating external force to be applied to the sample screw; and an extensometer including a stationary frame with twist detecting means for detecting a twist angle of the bolt by abutting to the tip end of the bolt, a movable frame rotatable with respect to the stationary frame in accordance with axial displacement of the head of the bolt and displacement detecting means for detecting elongation of the bolt in accordance with rotation of the movable frame.

2. An apparatus for testing performance of a screw as claimed in claim 1, wherein said nut tightening means is an electromotive reduction gear system.

3. An apparatus for testing performance of a screw as claimed in claim 2, wherein the external force generating means is a hydraulic system controlled by a computer consisting of a hydraulic power unit and a hydraulic cylinder.

4. An apparatus for testing performance of a screw as claimed in claim 2, further comprising a processing unit for inputting and operating each data of the thread torque, the bearing torque, said clamping torque, the axial tension, the bolt extension and the twist angle, outputting a result of the operation to a record display device, and feedback controlling the nut tightening means and said external force generating means in accordance with the result of the operation.

5. An apparatus for testing performance of a screw as claimed in claim 2, further comprising electronic control means for controlling said electromotive reduction gear system.

6. An apparatus for testing performance of a screw as claimed in claim 5, wherein said electronic control means is a computer.

7. An apparatus for testing performance of a screw as claimed in claim 1, wherein the external force generating means is a hydraulic system controlled by a computer consisting of a hydraulic power unit and a hydraulic cylinder.

8. An apparatus for testing performance of a screw as claimed in claim 7, further comprising a processing unit for inputting and operating each data of the thread torque, the bearing torque, said clamping torque, the axial tension, the bolt extension and the twist angle, outputting a result of the operation to a record display device, and feedback controlling the nut tightening means and said external force generating means in accordance with the result of the operation.

9. An apparatus for testing performance of a screw as claimed in claim 1, further comprising a processing unit for inputting and operating each data of the thread torque, the bearing torque, said clamping torque, the axial tension, the bolt extension and the twist angle, outputting a result of the operation to a record display device, and feedback controlling the nut tightening means and said external force generating means in accordance with the result of the operation.

10. A load cell comprising an opening having a bolt receiving bore for receiving a sample screw consisting of a bolt and a nut, a bolt retainer for engaging the head of the bolt to prevent the bolt from rotating when the nut is tightened on the bolt inserted in the bolt receiving bore, a bearing plate for engaging the nut tightened on the bolt, first strain detecting means provided on a shaft portion of the first frame for detecting thread torque and axial tension applied to the bolt retainer, second strain detecting means provided on a shaft portion of the second frame for detecting bearing torque and axial tension applied to the bearing plate and third strain detecting means provided on the third shaft portion connected to the first and the second shaft portions for detecting clamping torque consisting of the sum of the thread torque and the bearing torque and being such arranged that the bolt retainer and the bearing plate are separated from each other along the axis of the clamp screw by an external force.

11. A load cell as claimed in claim 10, wherein external diameters of the shaft portions of the first and the second frames and the third shaft portion do not exceed three times the external diameter of the sample screw, and the axial direction of said shaft portion is vertical.

12. A bolt displacement and twist detector comprising a stationary frame, twist detecting means fixed to the stationary frame and abutted to the tip end of a bolt for detecting a twist angle of the bolt, a movable frame rotated with respect to the stationary frame in accordance with axial displacement of the head of the bolt, the displacement detecting means for detecting elongation of the bolt in accordance with rotation of said movable frame.

* * * * *